(12) United States Patent
De Simone

(10) Patent No.: US 7,052,688 B2
(45) Date of Patent: May 30, 2006

(54) METHOD FOR PREVENTION AND/OR TREATMENT OF INFECTIONS AND INFLAMMATORY CONDITIONS USING A COMBINATION OF LACTIC ACID BACTERIA

(75) Inventor: Claudio De Simone, Ardea (IT)

(73) Assignee: VSL Pharmaceuticals, Inc., Gaithersburg, MD (US)

( * ) Notice: Subject to any disclaimer, the term of this patent is extended or adjusted under 35 U.S.C. 154(b) by 0 days.

(21) Appl. No.: 10/024,199

(22) Filed: Dec. 21, 2001

(65) Prior Publication Data

US 2002/0094328 A1    Jul. 18, 2002

Related U.S. Application Data

(63) Continuation of application No. PCT/IT00/00251, filed on Jun. 16, 2000.

(30) Foreign Application Priority Data

Jun. 21, 1999    (IT)    ............... RM99A0400

(51) Int. Cl.
*A01N 63/00*    (2006.01)
*C12N 1/00*    (2006.01)
*C12N 1/20*    (2006.01)

(52) U.S. Cl. ............... 424/93.45; 435/252.4; 435/252.9; 435/855; 435/856

(58) Field of Classification Search ............. 424/93.45, 424/93.3; 435/252.4, 252.9, 822, 853, 252.1
See application file for complete search history.

(56) References Cited

U.S. PATENT DOCUMENTS

| 5,176,911 | A | * | 1/1993 | Tosi et al. ............... 424/93.45 |
| 5,286,478 | A | * | 2/1994 | Persello ...................... 424/49 |
| 5,439,678 | A | * | 8/1995 | Dobrogosz et al. ...... 424/93.45 |
| 5,705,160 | A | | 1/1998 | Bruce et al. ............. 424/195.1 |
| 5,747,026 | A | * | 5/1998 | Crapo et al. ............... 424/94.3 |
| 5,895,648 | A | * | 4/1999 | Cavaliere Vesely et al. ......................... 424/93.4 |
| 6,159,724 | A | * | 12/2000 | Ehret ...................... 435/252.1 |
| 6,225,104 | B1 | * | 5/2001 | Cavaliere Vesely et al. ....................... 435/252.1 |
| 6,277,370 | B1 | * | 8/2001 | Cavaliere Ved. Vesely et al. ...................... 424/93.45 |
| 6,572,854 | B1 | | 6/2003 | DeSimone ............... 424/93.45 |

FOREIGN PATENT DOCUMENTS

| EP | 0 353 581 A | 2/1990 |
| EP | 0 555 618 A | 8/1993 |
| EP | 0 956 858 A | 11/1999 |
| WO | 99 42568 A | 8/1999 |

* cited by examiner

*Primary Examiner*—David M. Naff
*Assistant Examiner*—Deborah K. Ware
(74) *Attorney, Agent, or Firm*—Nixon & Vanderhye, PC

(57) ABSTRACT

The disclosure is of a combination of lactic acid bacteria comprising: (a) a first component consisting of at least one strain of $H_2O_2$-producing lactic acid bacteria; and (b) a second component consisting of at least one strain of arginine-utilizing lactic acid bacteria. The disclosure is also of the use of this combination for making a food supplement, a hygiene product or a pharmaceutical preparation for the prevention and/or treatment of infections and inflammatory conditions caused by bacteria, viruses or fungi, especially in the mouth, vagina, urethra, nose, eyes and ears.

16 Claims, No Drawings

METHOD FOR PREVENTION AND/OR TREATMENT OF INFECTIONS AND INFLAMMATORY CONDITIONS USING A COMBINATION OF LACTIC ACID BACTERIA

This application is the continuation of international application PCT/IT00/00251 filed 16 Jun. 2000, which designated the U.S.

The present invention relates to a combination of lactic acid bacteria and its use for making a food supplement, a hygiene product or a pharmaceutical preparation for the prevention and/or treatment of infections and inflammatory conditions caused by bacteria, viruses or fungi, especially in the mouth, vagina, urethra, nose, eyes and ears.

BACKGROUND OF THE INVENTION

Lactic acid bacteria are Gram-positive bacteria that produce lactic acid by the fermentation of glucose *Streptococcus thermophilus* is also included in this definition by convention.

It is well known that strains of lactic acid bacteria that produce $H_2O_2$ can act as regulators of the bacterial flora in body orifices and on mucous membranes. It has been demonstrated that $H_2O_2$-producing lactic acid bacteria can antagonize *E. coli, N. gonorrhoea, G. vaginalis, C. trachomatis, U. urealyticum* and *B. bivius*. However, these bacteria are only of limited benefit when used in medical practice. This can be seen from the fact that preparations based on lactic acid bacteria (e.g. vaginal pessaries) intended for the treatment of infections by the above microorganisms (e.g. vaginitis) are not held in high regard by doctors, who prefer to treat their patients with antibiotics or chemotherapeutic agents.

To the best of the inventor's knowledge, no antibacterial or flora-regulating action in body orifices and on mucous membranes has been attributed to arginine-utilizing lactic acid bacteria.

SUMMARY OF THE INVENTION

It has now been found surprisingly that the activity of $H_2O_2$-producing lactic acid bacteria is considerably potentiated by the addition of one or more strains of lactic acid bacteria that are capable of utilizing arginine. Arginine forms part of various small peptides found in biological fluids and it also occurs as free arginine. Many bacterial species utilize it for their own nutrition and growth. Arginine-utilizing lactic acid bacteria can therefore deprive other, pathogenic or potentially pathogenic bacteria of a certain quantity of arginine, which—though not enough to terminate their growth—makes them more susceptible to the action of the $H_2O_2$ produced by the lactic acid bacteria.

DETAILED DESCRIPTION OF THE INVENTION

The present invention therefore provides a combination of lactic acid bacteria comprising:
(a) a first component consisting of at least one strain of $H_2O_2$-producing lactic acid bacteria, and
(b) a second component consisting of at least one strain of arginine-utilizing lactic acid bacteria.

The strain of lactic acid bacteria in component (a) is preferably chosen from a group made up of the strains of the species *Lactobacillus crispatus, Lactobacillus salivarius* and *Lactobacillus casei*, while the strain of lactic acid bacteria in component (b) is chosen from a group made up of the strains of the species *Lactobacillus brevis, Lactobacillus gasseri* and *Lactobacillus fermentum*. More especially, the strain of lactic acid bacteria in component (b) is the *Lactobacillus brevis* CD2 strain deposited in the DSM-Deutsche Sammlung von Mikroorganismen und Zellkulturen GmbH, Braunschweig, Germany, on Feb. 6, 1998 with access number DSM 11988 under the Budapest Treaty, or mutants or derivatives thereof.

The ratio of the number of bacteria in component (a) to the number of bacteria in component (b) is preferably from 1:100 to 100:1, and more especially from 1:5 to 5:1, the most preferred ratio being 1:1.

The combination can be administered in the unit dosage form comprising from $1\times10^2$ to $5\times10^{11}$ bacteria of component (a) and from $1\times10^2$ to $5\times10^{11}$ bacteria of component (b), preferably $1\times10^9$ bacteria of component (a) and $3\times10^9$ bacteria of component (b).

The combination can also be administered in the form of tablets, sucking tablets, sweets, chewing gum, gelatin capsules, pessaries, suppositories and micro-enemas, as well as pellets, dental creams and gels, denture powders, mouthwashes, dentifrices, sprays, suspensions and ointments.

According to another embodiment of the invention, the combination additionally comprises at least one other strain of lactic acid bacteria chosen from a group made up of: *Lactobacillus acidophilus, Lactobacillus buchneri, Lactobacillus casei, Lactobacillus catenaforme, Lactobacillus cellobiosus, Lactobacillus crispatus, Lactobacillus curvatus, Lactobacillus delbrueckii, Lactobacillus jensenii, Lactobacillus leichmannii, Lactobacillus minutus, Lactobacillus plantarum, Lactobacillus salivarius, Lactobacillus brevis, Lactobacillus gasseri, Lactobacillus fermentum, Bifidobacterium adolescentis, Bifidobacterium angulatum, Bifidobacterium bifidum, Bifidobacterium breve, Bifidobacterium catenulatum, Bifidobacterium dentium, Bifidobacterium eriksonii, Bifidobacterium infantis, Bifidobacterium longum, Bifidobacterium plantarum* and *Streptococcus thermophilus*.

The combination can also comprise vitamins, quaternary ammonium bases, mineral salts, antioxidants and anti-plaque agents.

The invention also relates to the use of a combination of lactic acid bacteria comprising:
(a) a first component consisting of at least one strain of $H_2O_2$-producing lactic acid bacteria and
(b) a second component consisting of at least one strain of arginine-utilizing lactic acid bacteria, for making a food supplement, a hygiene product or a pharmaceutical preparation for the prevention and/or treatment of infections and inflammatory conditions caused by bacteria, viruses or fungi, especially in the mouth, vagina, urethra, nose, eyes and ears. These infections and inflammatory conditions include gingivitis, periodontitis, mucositis and stomatitis caused by drugs and/or physical agents, Behçet's syndrome, diakeratosis of the oral cavity, glossitis, sore throat, sialadenitis, sialolithiasis, pemphigus, *Lichen planus*, Sjögren's syndrome, vaginosis, vaginitis, urethritis, prostatitis, proctitis, otitis, conjunctivitis, rhinitis, sinusitis, leucoplakia, aphthae, herpes, and infections with *Helicobacter pilori* in the oral cavity.

The combination can also be used to advantage for the treatment of the oral cavity as an oral deodorant, antiinflammatory, anti-caries and/or anti-plaque agent.

The following examples serve to illustrate the various aspects of the invention in more detail but should not be construed as in any way limiting the invention.

EXAMPLE 1

The inhibitory effect of: $H_2O_2$-producing lactic acid bacteria (Component A); arginine-utilizing lactic acid bacteria (Component B); and the combination of the two strains, specifically in the ratio 1:1 (Combination AB); on the growth of potentially pathogenic bacteria was evaluated.

Briefly, the culture of lactic acid bacteria to be tested was first adjusted to a neutral pH, because an acidic pH itself inhibits bacterial growth. The suspension was subjected to sterile filtration, and the filtrate was used to impregnate a number of discs of absorbent paper (30 μl of filtrate per disc). The discs were placed on a plate of selective growth medium that had been inoculated with 0.1 μl of *Gardnerella vaginalis* (a strain which causes vaginosis and which was isolated in a laboratory) together with a control disc that was impregnated only with 30 μl of distilled water. After incubation for 24 h at 37° C., the inhibition of the growth of the pathogens was evaluated by measuring the diameter of the halo around the disc in millimetres.

A second series of tests was carried out with *Streptococcus mutans* as the target pathogen, this species being the causative agent of dental plaque and caries.

The characterization of the bacteria as $H_2O_2$ producers was done by a classical benzidine peroxidase reaction, which reveals $H_2O_2$-producing colonies of bacteria by a blue coloration. The activity of arginine dehydrolase was determined to evaluate the ability of the lactic acid bacteria to utilize arginine (M. C. Manca de Nadra, Milchwissenschaft, 37 (1982) pp. 669–670].

The lactic acid bacteria were obtained from the American Type Culture Collection (ATCC), Rockville, USA.

| Bacterial strain | Halo of inhibition (anti-G. vaginalis activity, mm) |
|---|---|
| $H_2O_2$ producer (Component A) | |
| Lactobacillus crispatus (ATCC 39197) | 75 |
| Lactobacillus salivarius (ATCC 11741) | 60 |
| Lactobacillus crispatus + Lactobacillus salivarius | 63 |
| Arginine utilizer (Component B) | |
| Lactobacillus brevis (ATCC 14869) | 0 |
| Lactobacillus fermentum (ATCC 14931) | 2 |
| Lactobacillus brevis + Lactobacillus fermentum | 0 |
| Combination AB (ratio of A to B 1:1) | |
| Lactobacillus crispatus + Lactobacillus brevis | 112 |
| Lactobacillus crispatus + Lactobacillus fermentum | 100 |
| Lactobacillus salivarius + Lactobacillus brevis | 117 |
| Lactobacillus salivarius + Lactobacillus fermentum | 104 |

| Bacterial strain | Halo of inhibition (anti-S. mutans activity, mm) |
|---|---|
| $H_2O_2$ producer (Component A) | |
| Lactobacillus crispatus (ATCC 39197) | 98 |
| Lactobacillus salivarius (ATCC 11741) | 102 |
| Lactobacillus crispatus + Lactobacillus saiivarius | 99 |
| Arginine utilzer (Component B) | |
| Lactobacillus brevis (ATCC 14869) | 0 |
| Lactobacillus fermentum (ATCC 14931) | 1 |
| Lactobacillus brevis + Lactobacilius fermentum | 1 |
| Combination AB (ratio of A to B 1:1) | |
| Lactobacillus crispatus + Lactobacillus brevis | 118 |
| Lactobacilius crispatus + Lactobacillus fermentum | 126 |
| Lactobacillus salivarius + Lactobacillus brevis | 121 |
| Lactobacillus salivarius + Lactobacillus fermentum | 120 |

EXAMPLE 2

Sucking tablets with the following unit composition were prepared:

| Combination AB | |
|---|---|
| (Lactobacillus salivarius + Lactobacillus brevis, ratio 1:1) | 4000 million |
| Mannitol | 400 mg |
| Saccharin | 5 mg |
| Polyoxyethylene | 50 mg |
| Mg stearate | 15 mg |
| Talc | 25 mg |
| Silica | 5 mg |

These tablets were administered to four volunteers who were told not to clean their teeth or use chewing gum during the previous week. The subjects took three tablets a day for one week, after meals, allowing the tablets to dissolve in their mouth. Clinical evaluations were performed for both the dental plaque index and the gingival plaque index.

For the dental plaque the following scoring system was used on six teeth (first upper molar on the right; upper central incisor on the left; first upper premolar on the left; first lower molar on the left; lower central incisor on the right; first lower premolar on the right):

0—no plaque at all

1—no visible plaque

2—visible plaque

3—very obvious plaque.

The following scoring system was adopted for evaluating the gingival plaque, using the margin of the six teeth mentioned above:

0—no inflammation

1—slight inflammation

2—moderate inflammation, with bleeding on contact

3—marked inflammation, with a tendency to spontaneous bleeding.

The combined data obtained for the six teeth of the four volunteers were as follows:

| Subject | Dental plaque index 0 | Dental plaque index 7 days | Gingival plaque index 0 | Gingival plaque index 7 days |
|---|---|---|---|---|
| No. 1 | 8 | 2 | 7 | 1 |
| No. 2 | 9 | 3 | 10 | 3 |
| No. 3 | 15 | 5 | 6 | 2 |
| No. 4 | 15 | 7 | 8 | 3 |

EXAMPLE 3

Four subjects with a clinical and histological diagnosis of recurrent aphthous ulcers were treated for ten days with six sucking tablets a day, whose composition is given in Example 2.

All the patients treated showed a complete cure of the ulcers at the end of the ten-day course, and none of them had new ulcers during the following month.

To improve the flavour and appearance of the bacterial combination AB, suitable colouring agents and sweeteners such as saccharin, mint oil and xylitol can be added, as is customary and well known to those skilled in the art.

The combination AB can be administered in the form of pellets, sweets, chewing gum, gelatin capsules, dental creams and gels, denture powders, mouthwashes, dentifrices, tablets, pessaries, suppositories, sprays, suspensions and micro-enemas.

EXAMPLE 4

Preparation of a toothpaste

Toothpaste base

Percentage composition:
| | |
|---|---|
| Calcium phosphate dihydrate | 37.5% |
| Glycerol (85% in water) | 30.0% |
| Flavour (peppermint oil) | 1.0% |
| Sodium carboxymethylcellulose | 1.0% |
| Purified water | 20.8% |
| Sodium saccharin (1% aq. solution) | 2.5% |
| Sodium lauryl sulphate | 2.0% |
| Purified water | 5.2% |
| | 100.0% |

Composition by weight:
| | |
|---|---|
| Calcium phosphate dihydrate | 337.5 g |
| Glycerol (85% in water) | 270.0 g |
| Flavour (peppermint oil) | 9.0 g |
| Sodium carboxymethylcellulose | 9.0 g |
| Purified water | 187.2 g |
| Sodium saccharin (1% aq. solution) | 22.5 g |
| Sodium lauryl sulphate | 18.0 g |
| Purified water | 48.8 g |
| | 900.0 g |

The glycerol was added to the calcium phosphate dihydrate, which had been ground and passed through a 50-mesh screen. The mixture was allowed to undergo hydration, giving a dense homogeneous paste. The flavour (1% of peppermint oil) was added at this point.

The sodium carboxymethylcellulose was hydrated in water overnight (concentration of 4.6% in purified water).

The solution of sodium saccharin was added to the resulting thick gel.

The polymer gel was poured into a mortar already containing the calcium phosphate that had been hydrated with glycerol, and the components were vigorously mixed.

An approximately 28% solution of sodium lauryl sulphate in purified water was prepared separately.

The sodium lauryl sulphate solution was then added to the thick dicalcium phosphate paste.

The resulting thick homogeneous paste, which had good rheological properties, was mixed for a few minutes and then refined by passing it through a refiner with rollers. This gave a snow-white homogeneous paste with a pleasant mint aroma.

38.5 g of lyophilized lactic acid bacteria (*L. salivarius*+*L. brevis*, 1:1; $10^{10}$ CFU/g) were passed through a 50-mesh screen and added in small portions to the rest (770 g) of the above toothpaste base. The resulting homogeneous paste had a slightly pale brown colour and a mint odour.

EXAMPLE 5

Preparation of Fast-Release Vaginal Tablets

Vaginal tablets coated with an effervescent layer were prepared by wet granulation. The tablets weighed 2100 mg each and contained 100 mg of the combination of lactic acid bacteria as the active substance.

Each vaginal tablet had the following composition:

| | |
|---|---|
| Lyophilized and screened lactic acid bacteria (30 × $10^9$ of *L. brevis*, 30 × $10^9$ of *L. salivarius* and 90 × $10^9$ of *L. plantarum* per gram) | 100.0 mg |
| Lactose | 1368.0 mg |
| Cornstarch | 246.0 mg |
| Adipic acid | 192.0 mg |
| Sodium bicarbonate | 150.0 mg |
| Magnesium stearate | 30.0 mg |
| Stearic acid | 9.0 mg |
| Colloidal silica | 5.0 mg |
| | 2100.0 mg |

The invention claimed is:

1. A method of inhibiting the growth of pathogenic bacteria, virus or fungi in a body cavity or orifice of a subject suffering from infectious or inflammatory conditions, comprising administering to a subject in need thereof an effective amount of a combination of lactic acid bacteria comprising a first component (a) consisting of at least one strain of $H_2O_2$-producing lactic acid bacteria, and a second component (b) consisting of at least one strain of arginine-utilizing lactic acid bacterial wherein component (a) is selected from the group consisting of the strains of the species *Lactobacillus crispatus*, *Lactobacillus salivarius* and *Lactobacillus casei*, and component (b) is selected from the group consisting of the strains of the species *Lactobacillus brevis* DSM 11988, a non-$H_2O_2$-producing *Lactobacillus gasseri* and *Lactobacillus fermentum*, provided that when component (a) is *Lactobacillus casei*, component (b) is not *Lactobacillus gasseri* or *Lactobacillus fermentum*, and when component (a) is *Lactobacillus crispatus*, component (b) is not *Lactobacillus fermentum*.

2. The method according to claim 1, in which the strain of lactic acid bacteria in component (b) is biologically pure *Lactobacillus brevis* DSM 11988.

3. The method according to claim 1, in which the ratio of the number of bacteria in component (a) to the number of bacteria in component (b) is from 1:100 to 100:1.

4. The method according to claim 3, in which the said ratio is from 1:5 to 5:1.

5. The method according to claim 4, in which the said ratio is from 1:1.

6. The method according to claim 1, comprising from $1\times10^2$ to $5\times10^{11}$ bacteria of component (a) and from $1\times10^2$ to $5\times10^{11}$ bacteria of component (b).

7. The method according to claim 6, comprising from $1\times10^9$ bacteria of component (a) and from $3\times10^9$ bacteria of component (b).

8. The method according to claim 1, wherein there is also administered at least one other strain of lactic acid bacteria selected from the group consisting of *Lactobacillus acidophilus, Lactobacillus buchneri, Lactobacillus catenaforme, Lactobacillus cellobiosus, Lactobacillus curvatus, Lactobacillus delbrueckii, Lactobacillus jensenii, Lactobacillus leichmannii, Lactobacillus minutus, Lactobacillus plantarum, Bifidobacterium adolescentis, Bifidobacterium angulatum, Bifidobacterium bifidum, Bifidobacterium breve, Bifidobacterium catenulatum, Bifidobacterium dentium, Bifidobacterium eriksonii, Bifidobacterium infantis, Bifidobacterium longum, Bifidobacterium plantarum* and *Streptococcus thermophilus*.

9. The method according to claim 1, wherein there are also administered vitamins, quatemary ammonium bases, mineral salts, antioxidants and anti-plaque agents with component (a) and component (b).

10. The method according to claim 10, wherein component (a) is *Lactobacillus crispatus* and component (b) is *Lactobacillus fermentum*.

11. The method according to claim 1, wherein component (a) is *Lactobacillus salivarius* and component (b) is *Lactobacillus fermentum*.

12. The method according to claim 10, wherein the ratio of the number of bacteria in component (a) to the number of bacteria in component (b) is 1:1.

13. The method according to claim 1, in which the infections and inflammatory conditions are selected from the group consisting of gingivitis, periodontitis, mucositis, stomatitis, Behçet's syndrome, diakeratosis of the oral cavity, glossitis, sore throat, sialadenitis, sialolithiasis, pemphigus, *Lichen planus*, Sjögren's syndrome, vaginosis, vaginitis, urethritis, prostatitis, proctitis, otitis, conjunctivitis, rhinitis, sinusitis, leucoplakia, aphthae, herpes, and infections of *Heliobacter pilori* in the oral cavity.

14. The method according to claim 1 wherein the combination is applied to the subject's mouth, vagina, urethra, nose, eyes or ears.

15. The method according to claim 1, in which the combination is applied to an oral cavity as a deodorant, anti-inflammatory, anti-caries or anti-plaque agent.

16. A method of inhibiting the growth of pathogenic bacteria, virus or fungi in a body cavity or orifice of a subject suffering from infectious or inflammatory conditions comprising administering to a subject in need thereof an effective amount of a combination of lactic acid bacteria comprising a first component (a) consisting of at least one strain of $H_2O_2$-producing lactic acid bacteria, and a second component (b) consisting of at least one strain of arginine-utilizing lactic acid bacterial wherein component (a) is selected from the group consisting of the strains of the species *Lactobacillus crispatus, Lactobacillus salivarius* and *Lactobacillus casei*, and component (b) is *Lactobacillus brevis* DSM 11988.

* * * * *